(12) United States Patent
Oei

(10) Patent No.: US 7,765,646 B2
(45) Date of Patent: Aug. 3, 2010

(54) INSTRUMENT FOR MANUAL OPERATION

(75) Inventor: San Tiong Oei, Overveen (NL)

(73) Assignee: Sanesco B.V., JL Overveen (NL)

( * ) Notice: Subject to any disclaimer, the term of this patent is extended or adjusted under 35 U.S.C. 154(b) by 484 days.

(21) Appl. No.: 11/568,143

(22) PCT Filed: Apr. 12, 2005

(86) PCT No.: PCT/NL2005/000277

§ 371 (c)(1),
(2), (4) Date: Jul. 23, 2007

(87) PCT Pub. No.: WO2005/102614

PCT Pub. Date: Nov. 3, 2005

(65) Prior Publication Data

US 2008/0033250 A1    Feb. 7, 2008

(30) Foreign Application Priority Data

Apr. 20, 2004    (NL)    .................... 1025985

(51) Int. Cl.
    B25G 1/00    (2006.01)
(52) U.S. Cl. .......................... 16/436; 16/430
(58) Field of Classification Search .................... 16/436,
    16/430, 431, DIG. 12, DIG. 19; 132/321,
    132/328, 329; 15/143.1, 111, 167.1, 105,
    15/161; 401/6, 7, 57, 8; 433/114, 141, 143,
    433/146–148; 604/164.12; 606/167, 166,
    606/53, 205, 174, 207, 140, 141; D7/688,
    D7/691, 368, 369, 393–395; D19/35, 41,
    D19/47–51; D8/107
See application file for complete search history.

(56) References Cited

U.S. PATENT DOCUMENTS

| 2,390,544 | A |   | 12/1945 | Lamb |
| 2,741,248 | A | * | 4/1956  | Woodhall ................... 606/176 |
| 4,780,924 | A | * | 11/1988 | Hansen et al. ............. 15/176.1 |
| 5,100,391 | A | * | 3/1992  | Schutte et al. .............. 606/167 |
| 5,586,989 | A |   | 12/1996 | Bray, Jr. |
| 5,737,803 | A | * | 4/1998  | Tisdale ........................ 16/430 |
| 5,836,958 | A | * | 11/1998 | Ralph ......................... 606/160 |
| 6,094,780 | A | * | 8/2000  | McGlothlin et al. ........... 16/430 |

(Continued)

FOREIGN PATENT DOCUMENTS

CH    615339 A    *    1/1980

(Continued)

Primary Examiner—Chuck Y. Mah
(74) Attorney, Agent, or Firm—Henry M. Feiereisen; Ursula B. Day

(57) ABSTRACT

The present invention relates to an instrument for manual operation (1) comprising a stem (2), an attendant member (3) disposed at a distal end of the stem (2), and a hand grip (4) disposed at a proximal end of the stem (2), having a substantially round shape and being fixed in the extended direction of the stem (2), wherein the stem (2) is placed eccentrically in relation to the hand grip (4), such that the body of the hand grip (4) has an axis that runs next to the axis of the body of the stem (2), at a side away from the attendant member (3), wherein at the functional side of the attendant member (3), the hand grip (4) possesses a first curve (5) and at the side opposite the functional side of the attendant member possesses a second curve (6) that differs from the first curve.

3 Claims, 1 Drawing Sheet

U.S. PATENT DOCUMENTS

| | | | |
|---|---|---|---|
| 6,099,538 A * | 8/2000 | Moses et al. | 606/144 |
| 6,530,125 B2 * | 3/2003 | Shippert | 16/430 |
| 7,523,525 B2 * | 4/2009 | Lawless | 16/430 |
| 2003/0009854 A1 | 1/2003 | Shippert | |

FOREIGN PATENT DOCUMENTS

| | | |
|---|---|---|
| DE | 24 55 625 A | 5/1976 |
| DE | 10209643 A1 * | 9/2003 |

* cited by examiner

INSTRUMENT FOR MANUAL OPERATION

BACKGROUND OF THE INVENTION

The invention relates to an instrument for manual operation comprising a stem, an attendant member disposed at a distal end of the stem, and a hand grip having a substantially round shape disposed at a proximal end of the stem.

Such an instrument is known from practice and is employed in numerous situations. As examples could be mentioned gardening tools, carpenter's tools, (electrical) toothbrushes, paint scrapers and in general all the devices that are provided with a hand grip to facilitate handling.

Many of the instruments for manual operation have handgrips that are not ergonomically shaped. A handgrip is often held in one way, but occasionally objects need to be held in different grip attitudes (underarm, overarm, obliquely underarm and obliquely overarm). If tensile forces have to be exerted with the instrument, a good grip is vital.

Firstly, to avoid fatigue striking too quickly and secondly, to be able to exert the necessary force while spending as little energy as possible.

An instrument of the kind referred to in the preamble, wherein the hand grip is fixed in the extended direction of the stem, and in which the stem is placed eccentrically in relation to the hand grip, such that the body of the hand grip has an axis that runs next to the axis of the body of the stem, at a side away from the attendant member, is known from U.S. Pat. No. 5,586,989. This concerns a curette for microsurgical applications.

Hereinbelow the invention will be further elucidated by way of an example of a retractor to be used in surgery. However, the invention must not be considered to be limited to the example given below, but rather relates to all possible applications in which an instrument for manual operation can be employed.

The retractors that have been available on the surgical market for more than a century, have not changed for decades. For example, one retractor known from the prior art is shown in DE-A-2455625. Medical problems related to the supporting and locomotor apparatus are widespread in the health care sector due to, among other things, poor posture while performing surgery. Complaints of neck and shoulders are particularly prevalent. When holding open a wound, the assistant handling the retractor is called upon to exert (considerable) static forces. For the surgeon it is important that the wound be held open properly from the beginning of the surgical procedure to the end. This varies from several minutes to an hour.

SUMMARY OF THE INVENTION

The object of the invention is in general to provide an instrument for manual operation that rests in the hand comfortably, so that the problems outlined above can be avoided.

To this end, the instrument according to the invention is characterized in that at the functional side of the attendant member, the hand grip possesses a first curve and at the side opposite the functional side of the attendant member it possesses a second curve that differs from the first curve. Due to this provision, the instrument rests in the hands comfortably, affording a firm grip in different positions, supporting the thumb and index finger while a tractive operation is being performed with the instrument.

Advantageously, the second curve has a stronger convexity than the first curve. When grasping the handgrip, it has a comfortable feel in all directions, facilitating good contact with the palm and fingers in all conceivable attitudes of holding the instrument.

The instrument according to the invention is particularly suitable for being applied as medical instrument and preferably as retractor, with the attendant member being embodied as hook.

BRIEF DESCRIPTION OF THE DRAWING

The invention will be further elucidated hereinbelow with reference to the drawing of a non-limiting exemplary embodiment of an instrument according to the invention.

The drawing shows.

DETAILED DESCRIPTION OF PREFERRED EMBODIMENTS

Figure 1:
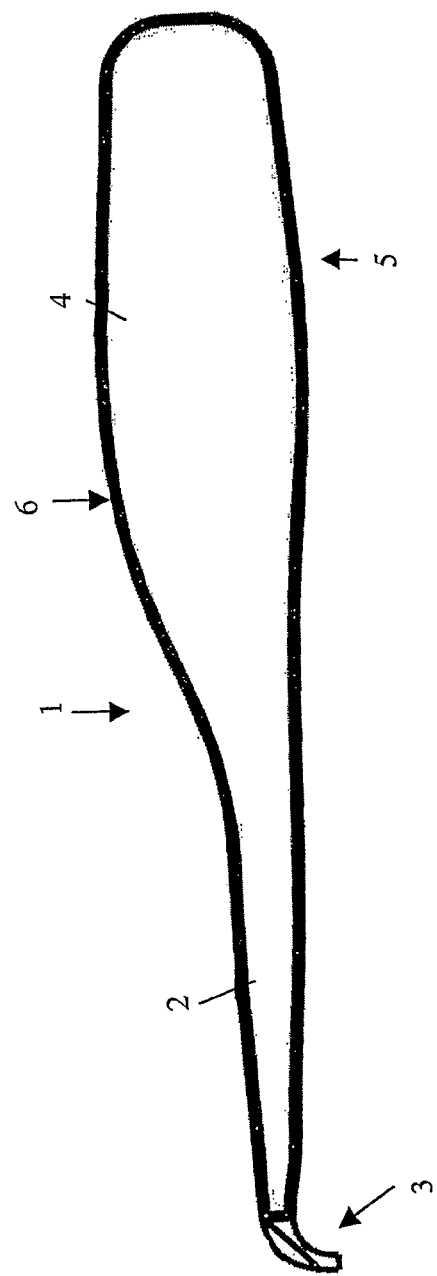
in FIG. 1, a side elevation of a retractor according to the invention.

Identical reference numerals refer to similar components.

Figure 2:
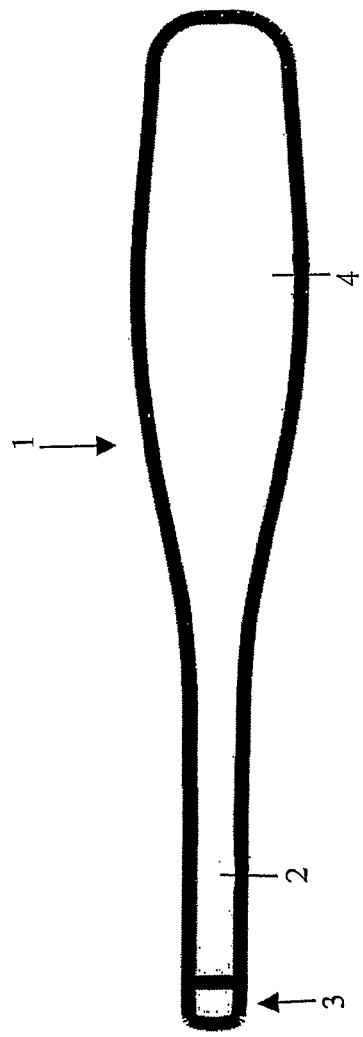
in FIG. 2, a top view of the retractor shown in FIG. 1, and in FIG. 3, a front view of the retractor shown in the FIGS. 1 and 2.
Figure 3:
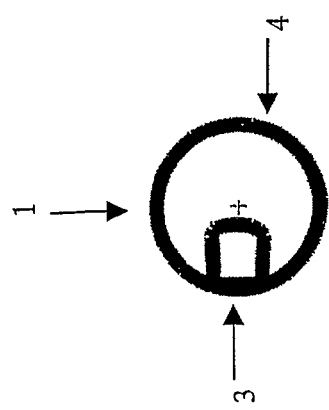

FIGS. 1, 2 and 3 show an instrument 1 for manual operation in the form of a retractor to be used in surgery.

This retractor 1 comprises a stem 2, an attendant member 3 placed at a distal end of the stem 2 and a hand grip 4, having substantially a round shape, placed at a proximal end of the stem 2.

FIG. 1 clearly shows that the stem 2 is placed eccentrically in relation to the hand grip 4, namely in a manner such that the body of the hand grip 4 has an axis that runs next to an axis of the body of the stem 2, at a side away from the attendant member 3. In a manner already known, the attendant member 3 is embodied as hook.

FIG. 1 also shows that the handgrip 4 possesses a first curve 5 at the side of the attendant member 3 and at the side opposite to the attendant member 3 a curve 6, that differs from the first curve 5. Advantageously, the second curve 6 has a stronger convexity than the first curve 5.

The handgrip of the retractor 1 according to the invention is always able to afford the user's thumb and index finger proper support.

The invention claimed is:

1. An instrument for manual operation, said instrument comprising:
    a stem defined by a longitudinal axis;
    an attendant member disposed at a distal end of the stem and having a functional side disposed laterally thereof; and
    a hand grip disposed at a proximal end of the stem and defined by a longitudinal axis, said hand grip having a substantially round shape cross-section and being fixed in an extended direction of the stem, wherein the longitudinal axis of the stem extends at a distance to the longitudinal axis of the hand grip so that the longitudinal axis of the hand grip extends offset to the longitudinal axis of the stem at a side away from the attendant member,
    wherein the hand grip has a first longitudinal curve at the functional side of the attendant member, and a second longitudinal curve extending at the side opposite the functional side of the attendant member and differing from the first curve, said second curve having convexity which is greater than a convexity of the first curve.

2. The instrument of claim 1 for use as a medical instrument.

3. The instrument of claim 1 for use as a retractor, with the attendant member having a hook-shaped configuration.

* * * * *